United States Patent
Bhambhani et al.

(10) Patent No.: US 10,429,129 B2
(45) Date of Patent: *Oct. 1, 2019

(54) METHOD OF MICROWAVE VACUUM DRYING SPHERICAL-SHAPED PELLETS OF BIOLOGICAL MATERIALS

(71) Applicant: Merck Sharp & Dohme Corp., Rahway, NJ (US)

(72) Inventors: Akhilesh Bhambhani, Doylestown, PA (US); Robert K. Evans, Bangor, ME (US); Jessica Sinacola, Collegeville, PA (US); Rebecca Lizzano, West Chester, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 27 days.

This patent is subject to a terminal disclaimer.

(21) Appl. No.: 15/029,062

(22) PCT Filed: Oct. 13, 2014

(86) PCT No.: PCT/US2014/060220
§ 371 (c)(1),
(2) Date: Apr. 13, 2016

(87) PCT Pub. No.: WO2015/057540
PCT Pub. Date: Apr. 23, 2015

(65) Prior Publication Data
US 2016/0252300 A1    Sep. 1, 2016

Related U.S. Application Data

(60) Provisional application No. 61/891,520, filed on Oct. 16, 2013.

(51) Int. Cl.
| C07K 1/00 | (2006.01) |
| F26B 5/04 | (2006.01) |
| A61K 39/15 | (2006.01) |
| C12N 7/00 | (2006.01) |
| A61K 9/00 | (2006.01) |
| A61K 39/00 | (2006.01) |

(52) U.S. Cl.
CPC ............ *F26B 5/048* (2013.01); *A61K 9/0014* (2013.01); *A61K 39/15* (2013.01); *C07K 1/00* (2013.01); *C12N 7/00* (2013.01); *A61K 2039/525* (2013.01); *C12N 2720/12334* (2013.01); *F26B 2200/08* (2013.01)

(58) Field of Classification Search
None
See application file for complete search history.

(56) References Cited

U.S. PATENT DOCUMENTS

| 4,389,794 A | 6/1983 | Bitterly |
| 4,664,924 A | 5/1987 | Sugisawn et al. |
| 4,809,596 A | 3/1989 | Akutsu et al. |
| 4,882,851 A | 11/1989 | Wennerstrum et al. |
| 5,565,318 A | 10/1996 | Walker et al. |
| 6,128,321 A | 10/2000 | Bennett et al. |
| 6,956,865 B1 | 10/2005 | Khaunte et al. |
| 9,782,470 B2 | 10/2017 | Bhambhani et al. |
| 2010/0015180 A1 | 1/2010 | Francon et al. |
| 2010/0218395 A1 | 9/2010 | Durante et al. |
| 2010/0260796 A1 | 10/2010 | Belin-Poput |
| 2010/0297231 A1 | 11/2010 | Vehring et al. |
| 2011/0064723 A1 | 3/2011 | Truong-Le et al. |
| 2011/0209354 A1 | 9/2011 | Durance et al. |
| 2011/0212130 A1 | 9/2011 | Yagodich et al. |
| 2011/0243988 A1 | 10/2011 | Ohtake et al. |
| 2012/0049412 A1* | 3/2012 | Middlebeek .............. A61J 3/10 264/299 |
| 2012/0291305 A1 | 11/2012 | Fu et al. |
| 2013/0189304 A1 | 7/2013 | Truong-Le |
| 2014/0017318 A1 | 1/2014 | O'Connell et al. |

FOREIGN PATENT DOCUMENTS

| WO | WO2002103407 A2 | 12/2002 |
| WO | WO 2008/092228 | * 8/2008 |
| WO | WO2008092228 | 8/2008 |
| WO | WO2009033285 A1 | 3/2009 |
| WO | WO2009049409 A1 | 4/2009 |
| WO | WO2009092703 A1 | 7/2009 |
| WO | WO2009109550 | 9/2009 |
| WO | WO2010125087 A1 | 11/2010 |

(Continued)

OTHER PUBLICATIONS

Wiggan et al. (Vaccine. Oct. 6, 2011; 29(43): 7456-7462) (Year: 2011).*
Fung et al. (Journal of Food Protection. vol. 43, No. 8, pp. 641-650, 1980) (Year: 1980).*
Siddharta et al. (Sci Rep. 2016; 6: 36619) (Year: 2016).*
Chiang et al., "A microwave applicator for uniform irradiation by circularly polarized waves in an anechoic chamber"; 2014, Rev. Sci. Instrum. 85:084703-1-084703-5.
Bhambhani, Akhilesh, Lyophilization Strategies for Development of a High-Concentration monoclonal antibody formulation: benefits and pitfalls, Am. Pharm. Review, 2010, 31-38, 13(1).

(Continued)

*Primary Examiner* — Sergio Coffa
(74) *Attorney, Agent, or Firm* — Letitia Walker; Laura M. Ginkel

(57) ABSTRACT

Methods for preparing dried pellets of biological materials are described. The pellets can have a substantially spherical shape and are prepared by freezing droplets of a liquid composition of a desired biological material on a solid surface followed by microwave vacuum drying the frozen droplets. These methods are useful for preparing dried pellets having a high concentration of a desired biological material, in particular a therapeutic protein or vaccine, and which have a faster reconstitution time than lyophilized powder cakes prepared in vials.

17 Claims, No Drawings

(56) References Cited

FOREIGN PATENT DOCUMENTS

| WO | WO 2013/010257 | * | 1/2013 |
| WO | WO2013010257 A1 | | 1/2013 |
| WO | WO 2013/066769 | * | 5/2013 |
| WO | WO2013066769 A1 | | 5/2013 |
| WO | 2014009328 A1 | | 1/2014 |
| WO | WO2015057541 A1 | | 4/2015 |
| WO | WO2015057548 A1 | | 4/2015 |

OTHER PUBLICATIONS

Dolan Jr, James Patrick et al., Use of Volumetric Heating to Improve Heat Transfer During Vial Freeze-Drying, https://theses.lib.vt.edu/theses/available, 1998, 1-171, 1.

Gupta, Chander Kanta et al., Stabilization of respiratory syncytial virus (RSV) against thermal inactivation and freeze-thaw cycles for development and control of RSV vaccines and immune globulin, Vaccine, 1996, 1417-1420, 14.

Ingram, M. et al., The survival of microbes in modulated high-frequency voltage fields, Proc. Soc. Appl., 1953, 69-87, 16.

Jones, Kathryn L. et al., Long-term storage of DNA-free RNA for use in vaccine studies, Biotechniques, 2007, 675-681, 43(5).

Law, T.J. et al., The Stabilizing Effect of Sucrose upon Respiratory Syncytial Virus Infectivity, Experimental Biology and Medicine, 1968, 515-518, 128.

McAdams, David et al., Spray drying and vaccine stabilization, Expert Rev. Vaccines, 2012, 1211-1219, 11(10).

Rigter, Alan et al., A Protective and Safe Intranasal RSV Vaccine Based on a Recombinant Prefusion-Like Form of the F Protein Bound to Bacterium-Like Particles, PLos One, 2013, e71072 (1-14), 8(8).

Seo, Jeong-Ah et al., Making monosaccharide and disaccharide sugar glasses by using microwave oven, Journal of Non-Crystalline Solids, 2004, 111-114, 333.

Tannock, Gregory A. et al., Freeze-Drying of Respiratory Syncytial Viruses for Transportation and Storage, J. Clin. Microbiol., 1987, 1769-1771, 25(9).

* cited by examiner

METHOD OF MICROWAVE VACUUM DRYING SPHERICAL-SHAPED PELLETS OF BIOLOGICAL MATERIALS

FIELD OF THE INVENTION

The present invention relates to methods for preparing dried pellets of biological materials that can be substantially spherical in shape and have fast reconstitution times in which a drying step is employed that utilizes microwave radiation. The resulting formulations are suitable for long-term storage.

BACKGROUND OF THE INVENTION

Biological materials such as cells, proteins and vaccines are frequently preserved by lyophilizing aliquots of a liquid composition containing the biological material. The lyophilization process involves freezing a liquid sample which is then subjected to a vacuum so that the ice in the frozen sample directly changes to water vapor or sublimes. After the removal of ice, the sample temperature is gradually increased (while still under vacuum) and water is desorbed from the remaining non-ice phase of the sample.

Lyophilized cakes of a biological material are prepared by aliquoting into a glass container a desired amount of the biological material, which is typically present in a buffered solution with appropriate stabilizers (i.e., a "formulation") and then subjecting the glass container containing the biological material to steps of cooling, freezing, annealing, primary drying and secondary drying. The glass container containing the dried biological material is typically stored for long periods of time at room temperature or under refrigerated conditions. The dried formulation containing the biological material is typically reconstituted by adding a liquid, usually water, to the glass container. Glass containers used for lyophilizing biological materials intended for use as therapeutics and vaccines typically have included glass vials and dual chamber injection devices, in which one chamber contains the lyophilized cake and the other chamber contains the reconstituting liquid.

Methods of lyophilizing biological materials in the form of spherically shaped pellets, (referred to as lyospheres or i.e., beads), have also been described. See, e.g., International Patent Application Publication Nos. WO 2009/092703, WO 2010/125087, and WO 2013/066769. In these methods, individual samples of the biological material are frozen and dried prior to placing a desired number of the dried samples into a storage container such as a glass vial. Historically, these methods relied on either (a) dispensing an aliquot of a liquid composition containing the desired amount of a biological material into a container of a cryogen such as liquid nitrogen, which results in direct contact of the biological material with the cryogen and/or (b) dispensing an aliquot of a liquid composition containing the biological material into a cavity present on a chilled solid plate, where the cavity contains the aliquot until it is frozen. Another approach, which is referred to as the die and punch method and uses a closed mold and compressive force to obtain a frozen pellet, suffers from a complex assembly design, leakage of fluid formation from the cavity and sticking of pellet to either the die or the punch.

Microwave vacuum-drying is a rapid method that can yield products, such as foods, plants and biological materials, with improved stability compared to air-dried and freeze-dried products. Because the drying is done under reduced pressure, the boiling point of water and the oxygen content of the atmosphere are lower, so food or medicinal components sensitive to oxidation and thermal degradation can be retained to a higher degree than by air-drying. See, e.g., U.S. Pat. Nos. 4,389,794; 4,664,924; 4,809,596; 4,882,851; 6,128,321; 6,956,865; and International Patent Application Publication Nos. WO 02/103407; WO 2009/033285; WO 2009/049409; and WO 2013/010257.

SUMMARY OF THE INVENTION

The present invention relates to a method for preparing dried pellets (<6% moisture) of a fluid formulation of a biological material comprising dispensing at least one liquid droplet onto a solid surface, freezing the droplet on the surface without contacting the droplet with a cryogenic substance and drying the frozen droplet using microwave vacuum drying to produce a dried pellet that can be substantially spherical in shape. The method may be used in a high throughput mode to prepare multiple dried pellets by simultaneously dispensing the desired number of droplets onto the solid surface, freezing the droplets and drying the frozen droplets. It has been surprisingly found that pellets prepared by the method of the invention from a liquid formulation having a high concentration of a biological material such as a protein therapeutic may be combined into a set of dried pellets that has a faster reconstitution time than a single lyophilized cake prepared by freezing and lyophilizing the same volume of the liquid formulation in a glass container. The method allows for drying by sublimation in short times, for example, less than 12 hours, and optimally in a range from 3 to 8 hours.

Accordingly, in one aspect of the invention, the present invention relates to a method of preparing a dried pellet of a biological material, comprising: a) dispensing an aliquot of a liquid composition comprising the biological material as a single droplet onto the surface of a metal plate, wherein the temperature of the metal plate is at −90° C. or below, in a manner that maintains the droplet as a single droplet as it contacts and freezes on the surface as a frozen pellet; and b) applying microwave radiation to the frozen pellet under a pressure below atmospheric pressure, e.g., in the range of 20 to 500 mTorr or 20 to 200 mTorr, to produce a dried pellet. In one embodiment, the surface is flat, i.e., has no cavity or wells in the area where the liquid composition is being applied. In another embodiment, the surface has a cavity or well in the area where the liquid composition is being applied. In an embodiment, the drying yield is greater than or equal to 50%.

In certain embodiments, the dispensing is performed with a dispensing tip at a speed and at a gap distance that prevents freezing of any portion of the aliquot in the tip and maintains the dispensed droplet in simultaneous contact with the surface of the metal plate and the open end of the dispensing tip until the droplet surface touching the plate is frozen. The dispensing speed can be selected from the group consisting of: about 3 ml/min to about 75 ml/min; about 5 ml/min to about 75 ml/min; about 3 ml/min to about 60 ml/min, about 20 ml/min to about 75 ml/min; and about 20 ml/min to about 60 ml/min. In certain sub-embodiments, the aliquot is 250 µl and the dispensing speed is between about 5 ml/min to about 75 ml/min, or wherein the aliquot is from 20 µl to 100 µl and the dispensing speed is between about 3 ml/min to about 60 ml/min.

In certain embodiments, the surface temperature of the metal plate is below −150° C. and the gap distance between the open end of the dispensing tip and the surface of the metal plate is between 0.1 cm and 0.5 cm or between 0.1 cm and 1 cm or between 0.1 cm and 0.75 cm. The surface temperature of the metal plate may be between about −180° C. and about −196° C. or between about −180° C. and about −273° C. In certain embodiments, the temperature of the pellet in step b) does not exceed 45° C. or 35° C.

In certain embodiments, the liquid composition comprises a total solute concentration of at least 20% on a weight by weight basis.

The microwave radiation is provided in an amount sufficient to heat and dry the sample without adversely affecting the integrity of the virus. In certain embodiments, the microwave radiation is applied with a power density of between 0.5 and 8 Kilowatts/kg. In certain embodiments, the microwave radiation is applied in a continuous or semi-continuous mode. In yet other embodiments, the microwave radiation is applied in a traveling wave format. In certain embodiments, the power applied during one or more cycles is such that 20% of the total power is applied during the first half of the cycle with the remaining 80% of the total power applied during the second half of the cycle. The ratio of power distribution between the power used in first half cycle and total drying power is usually in 15%-50% range.

The biological material can be selected from the group consisting of a purified antibody at a concentration in the liquid composition of at least 50 mg/ml or about 100 mg/ml; a vaccine (e.g., an enveloped live virus), a fusion protein, a polypeptide, and a peptide.

In certain embodiments, the method further comprises measuring the reconstitution time of the lyophilized pellet.

The present invention also relates to a container containing at least one dried pellet prepared by the methods described above. In certain embodiments, the dried pellet has a reconstitution time of less than 3 minutes or less than 2 minutes or less than 1 minute. In certain embodiments, the container is a glass vial. The container may comprise first and second compartments, with the at least one dried pellet present in the first compartment and a reconstitution liquid present in the second compartment.

Other embodiments, aspects and features of the present invention are either further described in or will be apparent from the ensuing description, examples, and appended claims.

DETAILED DESCRIPTION OF THE INVENTION

The present invention relates to a method of obtaining dried biologies or vaccine, either in a pellet form or cake form, through the application of microwave radiation in a traveling wave format to the frozen pellet or frozen cake of biologies/vaccines while maintaining the gross structure of frozen pellet or frozen cake using sublimation as the predominant drying mechanism. The frozen pellets of vaccine are obtained by aliquoting the formulation (10 μl to 500 μl) on a chilled mold/surface (Temperature <−100° C.). Similarly, the frozen cakes can be obtained by filling the container with the formulation and subjecting the container to freezing (mostly ≤40° C.) below the glass transition temperature at slow and fast freezing rate (0.1-20° C./min). The frozen formulations are then subjected to microwave radiation in a controlled manner in a vacuum chamber to obtain the dried pellets/cake with no visible sign of boiling. The present invention also pertains to the process of integrating the pellets dried in this manner with a device or a package.

It should be noted that integration of the pelletized (or lyosphere) form into the primary device after drying enables titration of the dose into the primary container, thus reducing active ingredient overage leading to greater final dose output for available bulk capacity. Microwave vacuum drying provides an alternate approach to freeze-drying samples in a device in a more efficient manner as microwave drying process is a radiation dominant process. Drying of lyosphere and/or frozen cake in cartridge/novel device can be done in <20% of time taken by conventional lyophilization without boiling the product.

As used herein, the term "sugar" refers to any of a group of water-soluble carbohydrates of relatively low molecular weight. The term sugar includes reducing sugars (such as fructose and maltose), non-reducing sugars (such as sucrose and trehalose), sugar alcohols (such as xylitol and sorbitol) and sugar acids (such as gluconic acid and tartaric acid). A "non-polymeric sugar" refers to mono-, di-, tri-, and oligomeric sugar molecules comprising at most six monomeric sugar molecules.

All ranges set forth herein are intended to be inclusive of the lower and upper limit of the range. All values set forth herein can vary by ±1%, ±2%, ±5%, ±10%, ±15%, or ±20%, the term "about" is also meant to encompass these variations.

The method of the present invention is also particularly useful for preparing dried spherical shaped pellets from compositions having a high solute concentration, e.g., concentrations above 20%. Such compositions may have high concentrations of sugars and other stabilizers, e.g., sucrose, trehalose, sucrose/trehalose mixtures, mannitol, dextrose, dextran and mixtures of such sugars. As demonstrated below, frozen spherical shaped droplets using the method described herein may be prepared from different types of compositions, including compositions with a low or high solute concentration, and dried using shorter drying cycles than if done in vials.

The method of the present invention may be utilized to prepare dried pellets of a variety of biological materials, including therapeutic proteins such as cytokines, enzymes and antibodies, as well as antigenic substances used in vaccines, such as peptides and proteins. The biological material is typically in a liquid composition that also contains one or more components that confer stability on the biological material during storage of the liquid formulation, as well as during and after the freezing and drying steps. This liquid composition is also referred to herein as a "liquid formulation, "pharmaceutical composition," "vaccine composition," and "vaccine formulation". Additional components that may be included as appropriate include pharmaceutically acceptable excipients, additives, diluents, buffers, sugars, amino acids (such as glycine, glutamine, asparagine, arginine or lysine), chelating agents, surfactants, polyols, bulking agents, stabilizers, cryoprotectants, lyoprotectants, solubilizers, emulsifiers, salts, adjuvants, tonicity enhancing agents (such as alkali metal halides, preferably sodium or potassium chloride, mannitol, sorbitol), delivery vehicles and anti-microbial preservatives. Acceptable formulation components for pharmaceutical preparations are nontoxic to recipients at the dosages and concentrations employed.

In some embodiments, the total excipient concentration in the composition used to prepare the pellets comprises 50% or less on a weight by weight basis (w/w) of excipients that have plasticizing effects, such as glycerol and sorbitol. Such excipients result in dried pellets that are fragile or spongy, which are undesirable characteristics for subsequent processing operations. The skilled artisan can readily identify other excipients that have plasticizing effects. In other embodiments, the pellets are prepared from compositions having at least 5% solute concentration w/w.

The buffer can be any carrier fluid suitable for dissolving and/or dispersing the substance to be carried. The buffer is usually selected from a pharmaceutically accepted buffer system. The preferred buffer is a pharmaceutically accepted buffer system with the ability to resist a change in pH upon addition of acid, base, inorganic compound, organic compound or other solvent or diluent. Buffering components, such as phosphate and citrate, are included to control the pH of the enveloped virus vaccine-containing solution, as well as to adjust the solution osmolarity. The buffer concentration may range from about 5 mM to about 2 M, with the pH of the solution adjusted to a range from about pH 4 to about pH 10.

A pharmaceutically acceptable buffer may be selected from the group consisting of potassium phosphate, sodium phosphate, sodium acetate, histidine, HEPES, Tris, Bis-Tris, imidazole, sodium citrate, sodium succinate, ammonium bicarbonate, and a carbonate. The buffer may comprise a pH ranging from about pH 4 to about pH 10, a pH ranging from about pH 6 to about pH 8, and also, a pH of about pH 6 to about pH 7.

The sugar is generally selected from monomeric and/or dimeric molecules, and in particular can be chosen from the group consisting of glucose, galactose, maltose, sucrose, trehalose, fructose, lactose, saccharose, mannitol, sorbitol, xylitol, dextran and combinations thereof. The amount of the sugar in the aqueous composition may range from 20-55% w/w, 20-50% w/w, 20-45% w/w, 25-45% w/w, 25-47.5% w/w, 25-40% w/w, 30-47.5% w/w, 30-40% w/w, 25-35% w/w or 27-30% w/w. Preferably, the amount of sugar is higher than 25% w/w, typically around 27-40% w/w.

The aqueous composition can further comprise surfactants, polymers, amino acids, and other pharmaceutically acceptable excipients. Polymer can be included to act as a stabilizer for the virus. Polymer concentration may range from about 0.1% to about 20% (w/v). Surfactants can be included to decrease the surface tension of the atomized droplets and to displace the virus molecules from the surface of the atomized droplets. Surfactants may also increase the solubility of other formulation components. Surfactant concentration may comprise about 0.005% to about 2% by weight of said virus vaccine-containing formulation. Plasticizers may be included to increase the interaction of the glassy matrix with the virus vaccine upon dehydration, thereby enhancing storage stability. See e.g., U.S. Pat. No. 7,101,693. The concentration of plasticizer in the present invention may comprise about 0.2% to about 5% by weight of the formulation. Divalent cations and amino acids can be included to stabilize the viral and to adjust the pH and the osmolarity of the solution. The divalent cation concentration may range from about 0.1 mM to about 100 mM and the amino acid concentration may range from about 0.1% to about 10% (w/v).

In one embodiment, the aqueous composition comprises a live or inactivated virus, a sugar, polymer, surfactant, amino acid and a buffer.

In another embodiment, the aqueous composition comprises a virus-like particle, a sugar, polymer, surfactant, amino acid and a buffer.

A polymer can be selected from the group consisting of gelatin, hydrolyzed gelatin, collagen, chondroitin sulfate, a sialated polysaccharide, water soluble polymers, polyvinyl pyrrolidone, actin, myosin, microtubules, dynein, kinetin, bovine serum albumin, human serum albumin, lactalbumin hydrolysate, and combinations thereof. A polymer is present at a concentration ranging from about 0.1% to about 20% (w/v). In one embodiment, the polymer is gelatin present at a concentration ranging from about 0.5% to about 5% (w/v).

A surfactant can be selected from the group consisting of polyethylene glycol, polypropylene glycol, polyethylene glycol/polypropylene glycol block copolymers, polyethylene glycol alkyl ethers, polyethylene glycol sorbitan monolaurate, polypropylene glycol alkyl ethers, polyethylene glycol/polypropylene glycol ether block copolymers, polyoxyethylenesorbitan monooleate, alkylarylsulfonates, phenylsulfonates, alkyl sulfates, alkyl sulfonates, alkyl ether sulfates, alkyl aryl ether sulfates, alkyl polyglycol ether phosphates, polyaryl phenyl ether phosphates, alkylsulfosuccinates, olefin sulfonates, paraffin sulfonates, petroleum sulfonates, taurides, sarcosides, fatty acids, alkylnaphthalenesulfonic acids, naphthalenesulfonic acids, lignosulfonic acids, condensates of sulfonated naphthalenes with formaldehyde and phenol, lignin-sulfite waste liquor, alkyl phosphates, quaternary ammonium compounds, amine, oxides, and betaines, wherein a surfactant is present at a concentration ranging from about 0.01% to about 2% by weight of said formulation. In one embodiment, the surfactant is polyoxyethylene sorbitan monooleate (polysorbate 80) at a concentration ranging from about 0.02% to about 0.5% by weight of said formulation.

A plasticizer can be selected from the group consisting of glycerol, dimethylsulfoxide (DMSO), propylene glycol, ethylene glycol, oligomeric polyethylene glycol, sorbitol, and combinations thereof, wherein a plasticizer is present at a concentration ranging from about 0.1% to about 5% by weight of said formulation.

Divalent cation can be selected from the group consisting of a pharmaceutically acceptable salt of magnesium, zinc, calcium, manganese, and their combinations thereof, at a concentration ranging from about 1 mM to about 5 mM. In one embodiment, the divalent cation is calcium at a concentration ranging from about 1 mM to about 5 mM.

Amino acid can be alanine, arginine, methionine, serine, lysine, histidine, glycine, glutamic acid, and combinations thereof, wherein an amino acid is present at a concentration ranging from about 0.1% to about 10% (w/v). Amino acids can also be provided by enzymatic digests of proteins. For example, NZ-Amine, an enzymatic digest of casein, can be used to provide a combination of amino acids. In one embodiment, the amino acid is arginine present at a concentration ranging from about 1% to about 8% (w/v).

In certain embodiments, the method of making dried pellets of a biological material according to the invention comprises loading an aliquot of a liquid composition (such as a liquid protein formulation) comprising the biological material into a dispensing tip and dispensing the aliquot onto a solid surface in such a way that the droplet remains intact while being dispensed. In one embodiment, the solid surface is a solid, flat surface. The term "solid, flat surface" means that there are no cavities or wells on the surface where the droplet is dispensed. In another embodiment, the solid surface has cavities or wells for dispensing the droplet.

In embodiments where a dispensing tip is used, dispensing tips useful in the present invention include those with a round open end, and a pointed open end, and can be obtained from Fisher Scientific, Beckman Coulter, BD syringes, ART Molecular Bioproducts, etc. Multiple dried pellets may be prepared simultaneously by loading simultaneously the desired number of aliquots of the liquid composition into a multichannel pipettor.

In one embodiment, the solid surface is the surface of a metal plate and is maintained at a temperature of −90° C. or lower. In some embodiments of the invention, the temperature of the metal plate is −150° C. or lower, or −180° C. or lower. In other embodiments, the temperature of the plate is within a range of about −90° C. to about −130° C., about −110° C. to about −150° C., about −150 C to about −195° C. or −180° C. to about −196° C. In one embodiment, the metal plate comprises a conductive, inert metal such as gold, silver, stainless steel, aluminum or copper. In a preferred embodiment, the metal plate is comprised of aluminum. In another preferred embodiment, the plate is stainless steel. In some embodiments, the metal plate is rectangular in shape, and in one preferred embodiment, the dimensions of the rectangular plate are 10 inches long×7 inches wide×0.4 inches thick.

The cold temperature of the metal plate can be maintained by placing the bottom surface of the metal plate in physical contact with a heat sink. In one preferred embodiment, the heat sink comprises a plurality of fins composed of a temperature conductive metal. In some embodiments, the fins are spaced about 0.25 inches apart along the bottom surface of the metal plate, with each fin having a length of at least about one inch. For a 10 inch×7 inch plate, the heat sink preferably comprises thirty, one inch long fins.

The fins may be physically connected to the bottom of the metal plate using any of a multitude of approaches well-known in the art, for example, using metal screws, welding, gluing with a cryoglue. In such an embodiment, the term "bottom surface" means the surface of the plate that is physically connected to the plurality of fins. Alternatively, the metal plate and heat sink may be fabricated from a single metal block and in such a case, the skilled artisan will understand that the bottom surface of the metal plate and heat sink form part of the same functional feature and thereby in physical contact with each other.

An example of a heat sink is one that is fabricated from a single metal block. This plate comprises a plurality of metal fins having one end in physical contact with the bottom surface of the metal plate, which rests on top of a metal reservoir containing a liquid cryogen such as liquid nitrogen. Other liquid cryogens that may be used in the heat sink include liquid propane, isopentane/hexane mixtures, argon and HFE-7100. The metal fins and reservoir are preferably made of the same conductive metal as used for the plate. Similar heat sinks may be purchased commercially, e.g., from M&M Metals, 1305 W Crosby Road, Carrollton, Tex.

In another embodiment, the solid surface is hydrophobic and is maintained above 0° C. during the dispensing step, and preferably between 4° C. and 25° C. The hydrophobic surface may comprise a chemically inert plastic such as polytetrafluoroethylene (PTFE), polypropylene and the like. The hydrophobic surface may be bonded to a different material or simply comprise the top surface of a thin film made using the hydrophobic material (e.g., PTFE, polypropylene). To freeze the liquid droplet, the film containing the dispensed droplet is chilled to a temperature that is below the freezing point of the liquid composition comprising the biological material, and preferably to a temperature of about 5° C. to 25° C. below the freezing point.

It is important to maintain the liquid droplet intact during the dispensing step. When the droplet is dispensed onto a cold metal surface (i.e., −90° C. or lower), one way of accomplishing this is to dispense the droplet at a dispensing speed and at a distance between top surface and the bottom of the dispensing tip (the "gap distance") that prevents the droplet from freezing while any portion of the droplet is still in the tip, and maintains the dispensed droplet in simultaneous contact with the top surface of the metal plate and the bottom of the dispensing tip. This allows the droplet to freeze from the bottom up as it contacts the cold metal surface.

The dispensing speed and gap distance will depend upon the volume of the liquid droplet, and the shape of the open end of the dispensing tip, and may be readily determined experimentally. For a 250 μl bead, for example, this speed could range from 0.2 second to 3.0 second. Similarly for 100 μl bead, for example, the dispensing speed could range from 0.1 second to 2 seconds. In the preferred embodiment, the dispensing speed is within the range of about 3 ml/min to about 75 ml/min, about 5 ml/min to about 75 ml/min, about 3 ml/min to about 60 ml/min, about 20 ml/min to about 75 ml/min, 20 ml/min to about 60 ml/min, respectively. A suitable dispensing speed for preparing 50 and 20 microliter droplets is 4.5 ml/min of a composition with low solute concentration (5%) and 9 ml/min for a composition with high solute (25%) concentration.

In an alternative embodiment, the gap distance (i.e., between the open end of the dispensing tip and the top surface) is high enough so that the dispensed drop is in contact only with the top surface of the cold metal plate. To maintain the intactness and spherical shape of the droplet, the temperature of the metal surface is preferably maintained well below −150° C. to ensure instantaneous freezing of the liquid droplet as it touches the surface. The gap distance will depend on the volume of the dispensed aliquot, but is usually at least 1 cm.

When the liquid droplet is dispensed onto a hydrophobic surface, the droplet is typically maintained intact in a substantially spherical shape by choosing a volume for the aliquot that will remain intact as the droplet touches the surface.

In preferred embodiments, the dispensing tip or tips are connected to an automated dispensing unit capable of controlling the dispensing speed and the gap distance. Examples of automated dispensing units include the Biomek® FX Liquid Handling System and pipettors manufactured by Tecan.

In some embodiments, the method further comprises measuring the reconstitution time of the dried pellet. The term "reconstitution time" refers to the time that is required to completely dissolve a dried pellet, e.g., one prepared according to the present invention, or a lyophilized cake to produce a reconstituted liquid formulation that is clear.

After the pellets are frozen, microwave radiation is applied to the frozen pellet under a pressure below atmospheric pressure to produce a dried pellet of substantially spherical shape. In one embodiment, the frozen pellets are placed in a microwave vacuum drying apparatus chamber for drying. Microwave drying provides a unique opportunity to achieve faster sublimation and in some cases alter the stability profile of thermolabile viruses by the virtue of an alternate heat transfer and mass transfer mechanism to the traditional approach. Furthermore, freeze-drying is considered an expensive unit operation due to significant capital investment, utility requirements and lengthy drying times. The lengthy drying times in freeze-drying are attributed to the fact that product temperature cannot be directly controlled during the primary drying as it depends on properties of container, formulation, shelf temperature, and chamber pressure of freeze-dryer system. Thus, a highly skilled scientist is required to perform a number of time-consuming experimental studies to obtain optimal lyophilization cycles and in most cases, sub-optimal" or "conservative" lyophilization cycles are used to dry sensitive products. The low temperature of freeze drying also does not guarantee stability post-drying due to denaturation at interfaces, cold denaturation or other freezing and drying stresses.

The microwave vacuum drying apparatus can be an apparatus capable of providing microwave radiation and a vacuum. Suitable apparatuses are described in U.S. Patent Application Publication Nos. US20120291305, US20100218395, and International Patent Application Publication No. WO2013/010257. A suitable apparatus provides the required uniform drying at the required power application in the required time.

Microwaving refers to the use of non-ionizing electromagnetic radiation to actively induce the evaporation of polar molecules (e.g., water) from a biological composition. Microwaves are electromagnetic waves having operating frequencies anywhere from 0.3 GHz to 300 GHz. While frequencies anywhere within this range can be used, commercially available microwaves typically have frequencies of 2450 MHz and 915 MHz, both of which may be used, but 2450 MHz is preferred. The vibration of polar molecules in a constantly changing electrical field of microwave radiation increases the temperature of the system quickly. Increase of temperature is perhaps the most important factor associated with microwave radiation and the majority of the effects on biological materials are directly related to the heating effect.

A vacuum is pulled to produce a low pressure in the chamber of between 20 to 500 mTorr, 20 to 200 mTorr, 20-100 mTorr or 20-70 mTorr. Sublimation rate is directly proportional to the differential pressure between the ice-water interface and the chamber pressure and it is therefore preferred to use the highest achievable pressure differential and minimize the time and temperature required to dry the vaccine.

The level of vacuum also controls the temperature of the vaccine composition being dried. In certain embodiments, the reduced pressure also is utilized to ensure the temperature in the vacuum chamber during drying remains below 45° C. or 35° C.

Drying time is controlled by the amount of vacuum and the power applied to the vaccine composition in the chamber. The higher microwave power applied to the vaccine composition the shorter the required drying time, but if the power is too high for too long deactivation of a live virus can occur. Too low an application of microwave power applied to the vaccine composition is detrimental as it extends drying time. It is preferred to operate using the lowest vacuum pressure (and thus the lowest drying temperature) and the highest application of microwave power in the chamber provided the power is not applied to the extent to damage the vaccine composition being processed to complete the drying quickly while subjecting the vaccine composition to a minimum required drying temperature. In certain embodiments of the invention, the composition is sublimated in less than 12 hours. In other embodiments, the composition is sublimated in the range of 6 to 10 hours, or 3 to 8 hours.

The maximum output power of the microwave may vary in the range of 50 Watt (W) to 900 W per magnetron. Up to 8-16 magnetrons can be used. In one embodiment, the microwave maximum output power per magnetron may be 600 W. In another embodiment, the microwave maximum output power per magnetron may be 400 W (e.g., for a single run consisting of 50-200 vials).

Generally the microwave power applied will be in the range of between 0.5 and 8 KW/hr/Kg of the enveloped virus being dried. The use of low power application is not preferred as the process may become too slow. Application of high power, i.e., above about 8 KW/Kg of the vaccine composition makes controlling the uniformity of the drying process at low moisture content more difficult. Generally an application of microwave power of about 4 KW/Kg of the vaccine composition is preferred.

It is also important to ramp up the microwave power to maintain the integrity of the vaccine composition. This can be achieved by slowly increasing the power at short intervals. Slower ramp (2 W/min) is preferred over stepping the power at bigger time interval (e.g. it is preferred to ramp up the power by 10 W every 10 min then going from 100 W to 250 W after 2.5 hrs). Such a ramping approach, in comparison to stepping up the power significantly, allows for gradual sublimation without compromising the product quality. In certain embodiments, the total energy in the first half of the cycle is only 15%, 20%, 25%, or 30% of the total energy required to dry the system. The ratio of power distribution between the power used in first half cycle and total drying power is usually in 15%-50%, 15-30%, or 15-20% range. Generally, to achieve the ramp up in microwave power, an initial cycle consists of a single magnetron. Additional magnetrons are added to the system as additional cycles are run. In general, any number of cycles can be used to provide the required microwave radiation. In certain embodiments, 3 to 8 cycles are used, for example 5 cycles, the cycle times are generally 30 minutes to 2 hours, and the total microwave energy output is generally in the range of 0.75 kWh to 8.0 kWh and is a function of total number of vials and product intrinsic characteristics.

In certain embodiments, the microwave radiation is applied in a continuous or semi-continuous mode or a batch mode. This selection is contingent on the process and product requirement. Semi-continuous and continuous mode allows for higher throughput while batch process may be used for an established apparatus design or a limited number of vial required.

As discussed above, the reduced pressure ensures that the temperature in the chamber is less than 40-45° C. In one embodiment, the temperature of the product is monitored does not exceed 35° C. The product temperature can be monitored using an IR sensor or a thermal imaging camera.

In certain embodiments, the microwave radiation is applied in a traveling wave format. With a traveling wave applicator, microwaves passes once through sample. This results in better temperature control and uniform product drying. Less preferred is resonance cavity where microwaves pass multiple times through sample. This results in thermal runaway (i.e. overheating) as the sample dries. A single pass microwave allows for controlling the product temperature by limiting the interaction between product and microwave. In contrast, electric field overlap in the resonance cavity results in an uncontrolled interaction and often results in the formation of hot and cold spots, uneven heating, and uneven sublimation of the product.

Under the conditions described herein, the moisture content of the composition after drying is less than 6.0%, less than 5.5%, or less than 5.0%. As discussed below, the relatively high moisture content is not detrimental to the formulations of the invention.

After completion of drying, the dried pellets may be placed in a container for bulk storage, or aliquoted into desired end-use container. Bulk storage containers include, e.g., plastic trays, metal trays, bottles, foil bags, and the like. The desired end-use container may be configured to receive a liquid for reconstitution directly in the container, e.g., a vial, or commercially available dual chamber containers, such as a dual-chamber cartridge pen device, dual chamber foil packet, a plastic tube with two or more chambers and designed to readily mix two or more components immediately before administration of the therapeutic or vaccine in the pellet. Alternatively, the end-use container may be adapted to allow removal of a desired number of pellets, e.g., such as a bead dispenser, and the removed pellets are then reconstituted with liquid in a separate container.

The method of the present invention is particularly useful for preparing dried pellets from liquid formulations having a high concentration of a therapeutic antibody, e.g. 50 mg/ml or more, and that has a reconstitution time of less than 3 minutes, preferably less than 2 min. The dried pellet is typically stable for at least 1 month at room temperature (e.g., 25° C.), and preferably at least 6 months at room temperature (e.g., 25° C.). Upon reconstitution, the formulation is suitable for parenteral administration such as intraveneous, intramuscular, intraperitoneal or subcutaneous injection.

The dried pellets prepared by the method of the present invention can be easily integrated into a variety of dosage sizes by choosing the volume of the droplet used to prepare each pellet and the number of pellets added to a single or multiple dosage container or delivery device. Also, the invention readily enables the preparation of combination therapeutic or immunogenic products, in which dried pellets comprising one biological material are combined in a single container with dried pellets comprising a different biological material. For example, pellets prepared from different antigen compositions, such as measles, mumps, rubella, and varicella, may be combined in a single container to obtain a multi-component vaccine. This allows the different antigens to remain separate until reconstitution, which can increase shelf-life of the vaccine. Similarly, combination products may contain separate antigen-comprising pellets and adjuvant-comprising pellets. Another example would be a combination of pellets comprising a protein with pellets comprising a peptide.

The following examples serve only to illustrate the invention and its practice. The examples are not to be construed as limitations on the scope or spirit of the invention.

EXAMPLES

Example 1: Evaluation of the Compatibility of Two Enveloped Live Virus Vaccine Formulations (LVV1 and LVV2) in Lyospheres (100 µl) with Microwave Vacuum Drying (MVD) Vs. Lyophilization (Lyo) in a Monolayer Drying Format Materials and Methods:
Four clear Ziploc containers were filled with a monolayer of lyospheres formed by dispensing liquid composition containing LVV1 or LVV2 (in formulations containing 5% Sucrose, 2.5% Gelatin in Phosphate buffer pH 7 in presence and absence of 1% Urea, respectively) on a flat surface according to the methods described in International Patent Application Publication No. WO 2010/125087 and the following cycle microwave parameters were used:

1 magnetron, 400 W, 1 hr
2 magnetrons, 400 W each, 1 hrs.
3 magnetrons, 400 W each, 1 hrs.
4 magnetrons, 400 W each, 1.5 hrs
2 magnetrons, 400 W each, 1 hrs.
Total Drying Time: 5.5 hrs.

The same liquid compositions was freeze-dried for approx. 24 hours in the standard lyophilizer (FTS Lyostar II) and the beads were loaded in a monolayer format on a stainless steel tray at −50° C. Freeze-drying was achieved using a shelf temperature of 15° C. and 30 mTorr pressure.

The samples were stored at −20° C. prior to characterization using plaque and relative potency assay. Frozen samples were used as control. Furthermore, the final moisture content of the dried-beads was determined using Karl Fischer (KF) analysis.

Results and Conclusions:

Table 1 below shows the moisture content and drying yield (as obtained using a standard plaque assay) for LVV1 and LVV2 as a function of drying method.

TABLE 1

Comparison of MVD vs. lyophilization (Lyo) for live virus

| | Drying Method | % Moisture | % Drying Yield (by plaque) |
|---|---|---|---|
| LVV1 | MVD | 5.06 ± 0.01 | 54 ± 15 |
| | Lyo | 0.97 ± 0.02 | 76 ± 3 |
| LVV2 | MVD | 3.54 ± 0.01 | 72 ± 18 |
| | Lyo | 0.94 ± 0.01 | 85 ± 21 |

The results show that the MVD drying yield of LVV1 was near to but slightly lower than the drying yield for lyophilization, while for LVV2, the MVD drying yield was comparable to the lyophilization yield. Under the given experimental conditions (non-optimized MVD cycle), the moisture contents of the MVD dried samples were higher than the lyophilized samples. Despite the fact that a non-optimized MVD cycle was used; successful drying of 2 formulations of a very sensitive virus was achieved with much faster drying times (MVD 5.5 hours vs. lyophilization 24 hours).

Example 2: Microwave Vacuum Drying of LVV1 Beads to Achieve a Target Moisture Content of Approximately 3%

Materials and Methods:

LVV1 beads (100 µl), as described in Example 1, were dried by MVD in a single layer in 4 clear plastic containers. Once the cycle was complete, the material was transferred to four 50 mL conical tubes and stored @−70° C. prior to moisture measurements using the KF method. The final temperature of the material, as monitored using Infrared (IR) probe installed on the MVD unit, was approximately 25° C. The cycle parameters (Vacuum: 50-100 mTorr) are listed below:

1 magnetron, 400 W 1.5 hrs
2 magnetrons, 400 W each 1.5 hrs
3 magnetrons, 400 W each 2 hrs
2 magnetrons, 400 W each 1 hrs Results and Conclusions:

In this study the moisture of active beads was tuned from 5.06% to 2.89-3.48% (see table 2) by altering the MVD cycle, showing that the final moisture content of LVV1 beads can be altered as a function of cycle parameters while maintaining a threshold terminal temperature of 25° C.

TABLE 2

Moisture content of live virus dried by MVD

| Sample | % Moisture |
|---|---|
| 1 | 3.17 |
| 2 | 2.89 |

TABLE 2-continued Moisture content of live virus dried by MVD

| Sample | % Moisture |
|---|---|
| 3 | 3.48 |
| 4 | 3.10 |

Example 3: MVD-Drying of High Viscosity Lyospheres Comprising Formulations Used for Oral Disintegrating Tablets (ODTs)

Materials and Methods:

250 μL beads were made using a lyosphere-making machine (see International Patent Application Publication No. WO 2010/125087) in the following four formulations.

1. 1% BS100 Gelatin, 8% Mannitol
2. 2% BS100 Gelatin, 8% Mannitol
3. 2% BS100 Gelatin, 2% Sol P Gelatin 3% Mannitol
4. 8% Sol P Gelatin, 9% Mannitol All four formulations were loaded into a microwave apparatus in clear plastic containers. The cycle parameters for drying of ODTs is listed below.

1 magnetron, 350 W, 1.5 hrs
2 magnetrons, 230 W each 2 hrs
3 magnetrons, 230 W each 1 hr
3 magnetrons, 350 W each 1 hr
4 magnetrons, 350 W each 1 hr
4 magnetrons, 470 W each 0.5 hr Results and Conclusions:

MVD was performed under a vacuum of 50-120 mTorr. The corresponding cycle parameters are shown in Table 3 below.

TABLE 3

Cycle parameters

| Formulation | Microwave Cycle | Final Temp | Moisture |
|---|---|---|---|
| 1 | 1% BS100 Gelatin 8% Mannitol | 1 magnetron, 350 W, 1.5 hrs | 25° C. | — |
| 2 | 2% BS100 Gelatin 8% Mannitol | 2 magnetrons, 230 W each 2 hrs | 25° C. | — |
| 3 | 2% BS100 Gelatin 2% Sol P Gelatin 3% Mannitol | 3 magnetrons, 230 W each 1 hr | 19° C. | — |
| 4 | 8% Sol P Gelatin 9% Mannitol | 3 magnetrons, 350 W each 1 hr 4 magnetrons, 350 W each 1 hr 4 magnetrons, 470 W each 0.5 hr | 26° C. | 4.1% |

The results show that the three formulations containing low gelatin (formulations 1-3) collapsed upon storage at room temperature due to high moisture content while a formulation with a higher gelatin concentration (formulation 4) maintained its shape upon storage at room temperature. Further experiments revealed that collapse of ODT formulations 1-3 was eliminated by extending the drying time at 500 W and increasing the terminal temperature of the formulations to 30° C. Thus, all four ODT formulations can be potentially dried using MVD.

Example 4: MVD Drying of Rotavirus Vaccines

Materials and Methods:

20 μl beads containing live rotavirus were made using automated lyosphere equipment (See International Patent Application Publication No. WO2013/066769). Two different formulations were tested as described below:

Formulation 1: 5% Sucrose, 5% Glycine, 50 mM Histidine, 50 mM Arginine, 0.01% PS80 (polysorbate 80), pH 7.2 and Formulation 2: 6% Sucrose, 10% Mannitol, 5 mM $CaCl_2$, 25 mM Histidine, 25 mM Arginine, 0.01% PS80, pH 7.2.

These formulations were dried in a monolayer format using either MVD (Total power 2 KWh; Time=7 hrs 20 min, $T_{end}$=25-28° C.) or freeze-drying (annealing at −20° C. and primary drying at 15° C./30 mTorr for 24 hrs). Dried beads were analyzed using Rotavirus Multivalent Quantitative-Polymerase Chain Reaction Based Potency Assay (M-QPA). See Ranheim et al., 2006, J. Virol. Methods, 131:193-201.

The drying parameters used for MVD and freeze-drying are listed in Table 4 below:

TABLE 4

MVD Cycle Parameters
MVD Cycle

| Watts | Magnetron | Length of Time |
|---|---|---|
| 200 W | 1 | 112 minutes |
| 200 W | 2 | 21 minutes |
| 200 W | 1 | 140 minutes |
| 200 W | 2 | 60 minutes |
| 200 W | 3 | 60 minutes |
| 200 W | 2 | 30 minutes |
| 200 W | 4 | 7 minutes |
| Held in Vacuum at total energy of 2 kwh | | 10 minutes |
| Terminal Temperature was 25° C. to 28° C. | | |

Lyo Cycle

Lyophilized Drying:

A pre-cooled shelf at −50° C. was used. Lyophilization parameters were set as shown in Tables 5 and 6: SP=setpoint

TABLE 5

Lyophilization parameters stage 1
Freezing/Thermal Treatment

|  | Step 1 | Step 2 | Step 3 |
|---|---|---|---|
| Temperature SP | −50° C. | −20° C. | −50° C. |
| Ramp Time | 16 min | 60 min | 60 min |
| Hold Time | 60 min | 120 min | 30 min |

TABLE 6

Lyophilization parameters stage 2
Drying

|  | Step 1 | Step 2 | Step 3 |
|---|---|---|---|
| Temperature SP | −50° C. | 15° C. | 15° C. |
| Ramp Time | 0 | 100 | 100 |
| Hold Time | 30 | 1440 | 1440 |
| Vacuum SP | 30 | 30 | 30 |

Results and Conclusions:

Table 7 below illustrates the total loss (i.e., natural log loss of potency) after drying combined with the potency loss after storage for 1 week at 37° C. for rotavirus reassortants as a function of formulation and drying method. The results show that for formulation 1, the MVD dried samples had comparable stability to the freeze-dried samples for reassortants G1, G3 and P1, while MVD dried samples were more stable than the freeze-dried samples for reassortants G2 and G4. For formulation 2, the results show that MVD dried samples were more stable than the freeze-dried samples for all five rotavirus reassortants.

TABLE 7

| Loss of rotavirus potency | | | | | | |
|---|---|---|---|---|---|---|
| Formulation | Drying Method | G1 | G2 | G3 | G4 | P1 |
| 1 | Freeze-drying | 0.99 | 1.03 | 2.03 | 1.22 | 1.11 |
| 1 | MVD | 0.91 | 0.34 | 2.21 | 0.87 | 1.30 |
| 2 | Freeze-drying* | 0.87 | 1.55 | 1.43 | 1.30 | 1.41 |
| 2 | MVD* | 0.19 | 0.63 | 0.67 | 0.57 | 0.26 |

*Some potency gains were observed upon incubation, presumably due to assay variability when testing the frozen liquid control.

In general, greater stability (especially for P1) was observed for formulation 2 compared to formulation 1. In summary, our findings show that MVD drying of lyospheres can provide enhanced stability for some rotavirus formulations, compared to freeze-drying.

Example 5: MVD Drying of Combination Vaccines

Materials and Methods:

50 μl beads of a combination vaccine having multiple enveloped viruses were made using automated lyosphere flat plate equipment, as described in Example 4, and three different test formulations as described below:

Formulation 1: 25% Trehalose, 3% Dextran, 25 mM Histidine, 25 mM Arginine, pH 6.2

Formulation 2: 25% Trehalose, 25 mM Histidine, 25 mM Arginine, pH 6.2

Formulation 3: 4% Sucrose, 3% Sorbitol, 10% Mannitol, 25 mM Histidine, 25 mM Arginine, pH 6.2

These formulations were dried in a monolayer format using either MVD (Total power 2 KWh; Time=7 hrs, $T_{end}$=25-26° C.) or freeze-drying (annealing at −20° C. and primary drying at 15° C./30 mTorr for 24 hrs). Dried beads were analyzed for virus potency using a plaque assay.

Details of the drying parameters used for MVD and freeze-drying are listed in Tables 8-10 below:

TABLE 8

| MVD Cycle (Vacuum < 100 mTorr) | | |
|---|---|---|
| Watts | Magnetrons | Total time |
| 200 W | 1 | 130 minutes |
| 200 W | 2 | 89 minutes |
| 200 W | 3 | 82 minutes |
| 200 W | 4 | 115 minutes |
| Under vacuum | | 20 minutes |
| Total energy 1.97240 kwh | | Temperature 25.5° C.-25.6° C. |

TABLE 9

| Lyo Cycle (Pre-cooled shelf at −50° C. was used) Freezing/Thermal Treatment | | | |
|---|---|---|---|
| | Step 1 | Step 2 | Step 3 |
| Temperature SP | −50° C. | −20° C. | −50° C. |
| Ramp Time | 0 | 60 min | 60 min |
| Hold Time | 60 min | 120 min | 15 min |

SP = Setpoint

TABLE 10

| Lyo Cycle Drying | | | |
|---|---|---|---|
| | Step 1 | Step 2 | Step 3 |
| Temperature SP | −50° C. | 15° C. | 15° C. |
| Ramp Time | 0 | 100 | 100 |
| Hold Time | 30 | 1440 | 1440 |
| Vacuum SP mTorr | 30 | 30 | 30 |

Results and Conclusions:

Table 11 shows the drying losses ($log_{10}$) for a combination vaccine having multiple enveloped viruses, as a function of formulation and drying method. The results show that MVD drying of this combination vaccine provides for drying losses that are approximately equal to or lower than drying losses obtained from freeze-drying.

TABLE 11

| Comparison of drying losses for a combination vaccine | | | | |
|---|---|---|---|---|
| Formulation | Drying Method | Virus 1 | Virus 2 | Virus 3 |
| 1 | Freeze-drying | 0.42 | 0.21 | 0.00 |
| | MVD | 0.11 | 0.11 | 0.00 |
| 2 | Freeze-drying | 0.10 | 0.45 | 0.00 |
| | MVD | 0.04 | 0.15 | 0.05 |
| 3 | Freeze-drying | 0.12 | 0.40 | 0.00 |
| | MVD | 0.07 | 0.36 | 0.00 |

Table 12 shows the accelerated stability losses ($log_{10}$) for the dried combination vaccine, as a function of drying method and formulation. The results show that MVD drying of this combination vaccine produces a product with a stability profile that is equal to or better than the stability of the freeze-dried product for formulations 1 and 2. Improved accelerated stability of MVD dried samples over freeze-dried samples is surprising as the moisture content of MVD dried formulation 2 was significantly higher than that of the freeze-dried formulation 2 (~5.5% for MVD vs. 0.9% for freeze-dried).

TABLE 12

| Comparison of accelerated stability losses for combination vaccine | | | | |
|---|---|---|---|---|
| Formulation | Drying Method | Virus 1 | Virus 2 | Virus 3 |
| 1 | Freeze-drying | 2.21 | 2.29 | 0.23 |
| | MVD | 1.01 | 1.04 | 0.23 |
| 2 | Freeze-drying | 1.62 | 1.92 | 0.18 |
| | MVD | 0.95 | 1.02 | 0.23 |
| 3 | Freeze-drying | 1.58 | 2.17 | 0.19 |
| | MVD | 2.27 | 2.37 | 0.37 |

These data reveal that MVD can successfully dry heat-sensitive products in bead form and achieve drying yields and stability profiles that are superior to what can be achieved with lyophilization.

Example 6: MVD Drying of an IgG1 Antibody

Materials and Methods:
Lyophilized spherical pellets of an anti-IL-23 antibody were prepared as described in U.S. provisional patent application Ser. No. 61/737,036, filed on Dec. 13, 2012.
Image:
50 μl beads made using flat plate approach as described in Examples 4 and 5.
Table 13 shows the MVD cycle used for drying the beads. Total energy was 2.99 kwh

TABLE 13

MVD cycles for antibody
MVD Cycle

| Watts | Magnetron | Length of Time |
|---|---|---|
| 200 W | 1 | 88 minutes |
| 200 W | 2 | 92 minutes |
| 200 W | 3 | 151 minutes |
| 200 W | 4 | 26 minutes |
| 200 W | 2 | 4 minutes |
| Held in Vacuum at total energy of 2 kwh | | 7 minutes |
| Terminal Temperature was 25.6° C. | | |

Lyophilization parameters were set as shown in Table 14. SP=Setpoint

TABLE 14

Lyophilization parameters for antibody

| | Step 1 | Step 2 | Step 3 |
|---|---|---|---|
| Freezing/Thermal Treatment | | | |
| Temperature SP | −50° C. | −20° C. | −50° C. |
| Ramp Time | 16 min | 60 min | 60 min |
| Hold Time | 60 min | 120 min | 30 min |
| Drying | | | |
| Temperature SP | −50° C. | 15° C. | 15° C. |
| Ramp Time | 0 | 100 | 100 |
| Hold Time | 30 | 1440 | 1440 |
| Vacuum SP mTorr | 30 | 30 | 30 |

Properties of reconstituted solutions prepared from the lyophilized pellets or the cake were characterized by visual inspection, optical density measurement of 100 μl samples at 350 nm, and concentration measurement with a UV-Vis spectrometer. The lyophilized pellets were reconstituted in the same volume of sterile water for injection (SWFI) as the starting volume of the pellets. Since dissolution of pellets causes a small expansion in volume, the total volume after reconstitution was higher compared to the starting volume. The antibody concentration in the reconstituted composition was lower than in the starting composition.

The time required to reconstitute the dried spherical pellets as compared to the same quantity of antibody in dried cake in the control vial was then determined Four dried pellets from each batch were transferred to a 2 ml type 1 glass vial and 200 microliters of SWFI was added to the vial. The same volume of SWFI was added to the control vial containing dried cake. All of the vials were rotated gently, and the reconstitution time was measured using a stop watch starting with the addition of the SWFI and ending with complete dissolution of all of the dried pellets or lyophilized cake, as determined by visual inspection. As shown in Table 15 below, the reconstitution time of the lyophilized cake was 16 minutes while reconstitution times was significantly lower for beads dried using MVD as well as freeze-drying.

DSC measurements: The thermal melting profile of the antibody in the reconstituted solutions was also characterized using Differential Scanning Calorimetry (DSC), with a TA instruments DSC Q2000 V23.10 Build 79 (Tzero pan; TA; Lot #603349; Cat #T110516, Tzero Hermetic lid; TA; Lot #603161; Cat #T110407).

HP-IEX: Stability of the antibody in these reconstituted solutions was characterized by high performance ion exchange chromatography (HP-IEX). HP-IEX detects chemical changes in the molecule by separating subpopulations of the same molecules based on their net charge. Any change in percentage of charged species compared to a reference material is measured.

HP-SEC: Aggregate content is a critical quality attribute for biologic drug products. Thus, the aggregate content in the reconstituted solutions was characterized by High Performance Size Exclusion chromatography (HP-SEC), can detect high molecular weight species by separating subpopulations of the same molecules based on their size.

Results:
During the 4 Magnetron cycle, translucent bubbles were noticed on the IgG1 formulation and the cycle was reduced to 2 magnetrons. After removing the beads, the IgG1 beads had translucent bubbles from some, but not all of the beads.

Conclusions:
Table 15 summarizes the results of analytical characterization

TABLE 15

| | (12.5% sucrose, 12.5% trehalose, 0.05% PS-80, 10 mM Histidine, pH 6.0)/ lyosphere in MVD | (12.5% sucrose, 12.5% trehalose, 0.05% PS-80, 10 mM Histidine, pH 6.0)/ lyosphere in Lyo | (7% sucrose, 0.05% PS-80, 10 mM Histidine, pH 6.0)/ lyosphere in Lyo | (7% sucrose, 0.05% PS-80, 10 mM Histidine, pH 6.0)/ lyosphere in MVD | (7% sucrose, 0.05% PS-80, 10 mM Histidine, pH 6.0)/ Histidine, pH 6.0)/ Pre-lyo Lyo cake | (12.5% sucrose, 12.5% trehalose, 0.05% PS-80, 10 mM Histidine, pH 6.0)/ Pre-lyo solution | (7% sucrose, 0.05% PS-80, 10 mM Histidine, pH 6.0)/ pre-lyo solution |
|---|---|---|---|---|---|---|---|
| Appearance | Some beads are half Clear/opaque some meltback | Opaque white beads | Opaque white beads | Opaque white beads | White cake | N/A | N/A |

TABLE 15-continued

|  | (12.5% sucrose, 12.5% trehalose, 0.05% PS-80, 10 mM Histidine, pH 6.0)/ lyosphere in MVD | (12.5% sucrose, 12.5% trehalose, 0.05% PS-80, 10 mM Histidine, pH 6.0)/ lyosphere in Lyo | (7% sucrose, 0.05% PS-80, 10 mM Histidine, pH 6.0)/ lyosphere in Lyo | (7% sucrose, 0.05% PS-80, 10 mM Histidine, pH 6.0)/ lyosphere in MVD | (7% sucrose, 0.05% PS-80, 10 mM Histidine, pH 6.0)/ Lyo cake | (12.5% sucrose, 12.5% trehalose, 0.05% PS-80, 10 mM Histidine, pH 6.0)/ Pre-lyo solution | (7% sucrose, 0.05% PS-80, 10 mM Histidine, pH 6.0)/ pre-lyo solution |
|---|---|---|---|---|---|---|---|
| Recon Time | 3 min 12 sec | 2 min 13 sec | 50 sec | 1 min 16 sec | 16 min | N/A | N/A |
| OD 350 nm | 0.061 | 0.065 | 0.090 | 0.070 | 0.083 | 0.066 | 0.031 |
| Concentration (mg/mL) | 74.6 | 71.2 | 82.7 | 83.1 | 90.0 | 111.4 | 100.2 |
| DSC | | | | | | | |
| Tonset (° C.) | 71.5 | 71.1 | 68.2 | 68.2 | 68.3 | 64.6 | 68.2 |
| Tm1 (° C.) | 75.5 | 75.2 | 72.7 | 72.9 | 73.1 | 71.2 | 72.6 |
| Tm2 (° C.) | 88.0 | 87.9 | 86.4 | 86.5 | 86.6 | 88.5 | 86.5 |
| HP-IEX | | | | | | | |
| Acidic Variants (%) | 10.3 | 10.3 | 10.1 | 10.0 | 10.0 | 11.1 | 10.2 |
| Main (%) | 61.8 | 61.2 | 61.5 | 62.0 | 61.7 | 48.7 | 60.9 |
| Basic Variants (%) | 3.8 | 3.8 | 3.8 | 3.7 | 3.8 | 4.5 | 3.8 |
| HP-SEC | | | | | | | |
| HMW Species (%) | 0.59 | 0.61 | 0.49 | 0.42 | 0.49 | 0.44 | 0.48 |
| Monomer (%) | 99.3 | 99.3 | 99.4 | 99.5 | 99.4 | 97.6 | 99.4 |
| LMW Species (%) | 0.12 | 0.13 | 0.12 | 0.12 | 0.11 | 1.99 | 0.12 |

The results show that MVD can be used to successfully dry IgG1 antibodies in lyospheres in less time than required for lyophilization and achieve the same quality of final product. The results also show that the reconstitution time of high concentration antibody formulations is significantly shorter for lyospheres than for a lyophilized cake in a vial.

While the foregoing specification teaches the principles of the present invention, with examples provided for the purpose of illustration, the practice of the invention encompasses all of the usual variations, adaptations and/or modifications that come within the scope of the following claims.

What is claimed is:

1. A method of preparing a dried pellet of an enveloped live virus, comprising:
   a) dispensing an aliquot of a liquid composition comprising the enveloped live virus as a single droplet onto a solid surface, wherein the temperature of the solid surface is at −90° C. or below, in a manner that maintains the droplet as a single droplet as it contacts and freezes on the surface as a frozen pellet;
   b) applying microwave radiation in a traveling wave format at a power in a range of between 0.5 and 8 KW/hr/Kg to the frozen pellet under a pressure below atmospheric pressure to produce a dried pellet;
wherein the drying yield, as obtained by a plaque assay, is greater than or equal to 50%.

2. The method of claim 1, wherein the solid surface is a flat surface.

3. The method of claim 1, wherein the solid surface has one or more cavities or wells for dispensing the liquid droplets.

4. The method of claim 1, wherein the dispensing is performed from a dispensing tip at a speed and at a gap distance that prevents freezing of any portion of the aliquot and maintains the dispensed droplet in simultaneous contact with the solid surface and the open end of the dispensing tip until the surface of the dispensed droplet touching the solid surface is frozen.

5. The method of claim 4, wherein the dispensing speed is selected from the group consisting of: about 3 ml/min to about 75 ml/min; about 5 ml/min to about 75 ml/min; about 3 ml/min to about 60 ml/min, about 20 ml/min to about 75 ml/min; and about 20 ml/min to about 60 ml/min.

6. The method of claim 4, wherein the surface temperature of the solid surface is below −150° C. and the gap distance between the open end of the dispensing tip and the solid surface is between 0.1 cm and 0.5 cm or between 0.1 cm and 1 cm or between 0.1 cm and 0.75 cm.

7. The method of claim 1, wherein the liquid composition comprises a total solute concentration of at least 20% on a weight by weight basis.

8. The method of claim 1, further comprising measuring the reconstitution time of the dried pellet.

9. The method according to claim 1, wherein the liquid composition is sublimated in less than 12 hours.

10. The method according to claim 1, wherein the pressure is in the range of 20 to 500 mTorr.

11. The method according to claim 1, wherein the temperature of the dried pellet in step b) does not exceed 45° C.

12. The method according to claim 1, wherein the microwave radiation is applied in a continuous or semi-continuous mode.

13. The method according to claim 1, wherein the liquid composition contains sugar in an amount chosen from the group that consists of the ranges 20-55% w/w, 20-50% w/w, 20-45% w/w, 25-45% w/w, 25-47.5% w/w, 25-40% w/w, 30-47.5% w/w, 30-40% w/w, 25-35% w/w or 27-30% w/w.

14. A container containing at least one dried pellet prepared by the method of claim 1.

15. The container of claim 14, wherein the dried pallet has a reconstruction time of less than 5 minutes or less than 2 minutes or less than 1 minute.

16. The container of claim 14, wherein the container is selected from glass vial, resin vials, plastic vials, dual cartridge device, or foil-pouch based devices vaccine.

17. The container of claim 14, wherein the moisture content of the liquid composition after drying is less than 60%.

* * * * *